United States Patent [19]

Hidaka et al.

[11] Patent Number: 4,801,458
[45] Date of Patent: Jan. 31, 1989

[54] SUSTAINED RELEASE PHARMACEUTICAL PLASTER

[75] Inventors: Osafumi Hidaka; Tomoki Sakai; Toyoaki Sakano, all of Tokyo, Japan

[73] Assignee: Teijin Limited, Osaka, Japan

[21] Appl. No.: 17,946

[22] PCT Filed: Jun. 23, 1986

[86] PCT No.: PCT/JP86/00317
§ 371 Date: Feb. 24, 1987
§ 102(e) Date: Feb. 24, 1987

[87] PCT Pub. No.: WO87/00046
PCT Pub. Date: Jan. 15, 1987

[30] Foreign Application Priority Data

Jun. 24, 1985 [JP] Japan ................ 60-135917

[51] Int. Cl.⁴ ............................. A61K 9/70
[52] U.S. Cl. .................... 424/443; 424/445; 424/448; 424/449
[58] Field of Search ........... 424/444, 448, 449, 443

[56] References Cited

U.S. PATENT DOCUMENTS 4,675,009 6/1987 Hymes et al. ................ 424/448
4,693,776 9/1987 Krampe et al. ................ 424/448
4,695,465 9/1987 Kigarata et al. ................ 424/448

FOREIGN PATENT DOCUMENTS 56-145215 11/1981 Japan .
8600317 2/1982 Japan .
57-31611 2/1982 Japan .
59-84815 5/1984 Japan .

OTHER PUBLICATIONS

Chemical Abstracts, vol. 101, 1984, 78875n-Sustained Release Transdermal Tapes Containing Hollow Fibers for Drug Transport, JP 5984855.

Primary Examiner—Thurman K. Page
Assistant Examiner—L. R. Horne
Attorney, Agent, or Firm—Sughrue, Mion, Zinn, Macpeak & Seas

[57] ABSTRACT

A sustained release pharmaceutical plaster which is characterized in that it is a pharmaceutical preparation mainly composed of an adhesive compound layer and a supporter which supports the adhesive compound layer, inside of which there is an arrangement of hollow fibers, that have radially arranged open pores, with their tubular hollows filled with medicines.

8 Claims, 1 Drawing Sheet

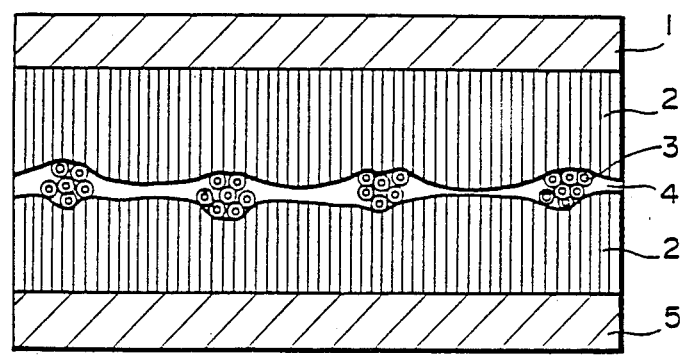

SUSTAINED RELEASE PHARMACEUTICAL PLASTER

TECHNICAL FIELD

The present invention relates to a sustained release pharmaceutical preparation for percutaneous administration use. More particularly, this invention relates to a sustained release pharmaceutical plaster mainly composed of an adhesive compound layer holding such hollow fibers of specific type that are made to contain medicinal substances in their tubular hollows and a supporter which supports said adhesive layer.

The sustained release pharmaceutical plaster of this invention is an excellent sustained release pharmaceutical plaster since it is perfectly good in sustained release of medicinal substances, rarely causes sweaty stuffiness or contact dermatitis when applied to the human body, and can be produced industrially with ease.

BACKGROUND OF THE ART

Active studies are being made from various angles to develop novel compounds having an outstanding efficaciousness, and at the same time to increase the pharmacological effectiveness of these novel chemical substances or of chemical substances which have already been in use as pharmaceuticals by changing the dosage form or by optimizing the dosage regimen.

For example, with the purpose of prolongating the duration time of medicines who have a short half-life period which is regarded as the parameter for the effective duration time of medicines in the body, there have been considerable activities to develop sustained release pharmaceuticals which are made to have a concentration between the minimum effective concentration or higher and the maximum safety concentration or lower, so that the effective ingredients may be absorbed into the human body in the whole range of effective blood concentration extending over a long period of time.

As examples of sustained release pharmaceuticals, there are pharmaceutical preparations in the form of a tape or a plaster which are made to contain a prescribed amount of medicines in their adhesive layers, having a specific size (Japanese Patent Laid-Open Publication Nos. 116011/'82 and 134020/'83).

Conventional tape or plaster preparations have problems. In case where it is desired to administer a pharmaceuticals as long as possible between the minimum effective concentration or higher and the maximum safety concentration or lower, they are simply made to have an increased concentration of medicines in the adhesive layer with the result of increasing the initial concentration of medicines absorbed into the human body or causing cutaneous diseases. If the diffusion rate of the medicines is lowered by changing the composition of an adhesive compound to slow down the adsorption rate of the medicines, the initial absorption concentration of the medicines decreases.

As another method of increasing the sustained release effect of tape and plaster preparations, there is a method to increase the thickness of an adhesive compound layer; however, this method is apt to raise such problems as to increase the skin irritation or to allow part of the adhesive compound to stick to the skin as the residue.

There is another method in which the concentration of medicines in the adhesive compound is lowered while the area of the plaster stuck to the skin is made larger. This method, however, is also confronted with problems of the inconvenience in the handling of the plaster, the enlargement of the undesirable irritation of the skin, and the limit of the site of application.

As the improved type of tape or plaster preparation, tere is one whose adhesive layer is made to contain microcapsules filled with medicines (Japanese Patent Publication No. 16566/'79); however, a plaster of this type requires complicated procedures in the course of its production and the sustained release of the medicines is not satisfactory enough.

There is still another type of tape and plaster, and it is a plaster which is designed to have its hollow fibers filled with medicines and then have these hollow fibers arranged on its outer surface which comes in contact with the skin upon which it is applied (Japanese Patent Laid-Open Publication No. 31611/'82). However, problems are also apt to be found with them by causing unpleasant irritation or eruption on the skin due to the extraordinary rise of the drug concentration at the site of its application where the skin is in direct contact with the drug. The plaster of this type can not be said to have enough sustained releasing function, either.

DISCLOSURE OF THE INVENTION

As the result of a laborious study made, after due reflection on the aforementioned faults, with the object of obtaining a sustained release pharmaceutical plaster with a definitely small area of effective application, which is able to release a desired amount of medicines by slow degrees for a long period of time, while suppresive of such side effects as sweaty stuffiness and contact dermatitis, and is capable of being produced with ease, the present inventor has found that a plaster having an adhesive layer, which is made to contain radially multiporous hollow fibers whose tubular hollows are filled with medicines, can fulfil the said object, and further that a higher excellent plaster can be obtained by filling the tubular hollows of the abovementioned hollow fibers with medicines which start evaporating when applied to the human body, placing thus medicine-filled hollow fibers inside the adhesive layer, and providing empty spaces around the hollow fibers, thus completing this invention.

To sum up the above, this invention relates to a sustained release pharmaceutical plaster which is characterized in that it is a pharmaceutical preparation mainly composed of an adhesive compound layer and a supporter which supports the adhesive compound layer, inside of which there is an arrangement of hollow fibers, that have radially arranged open pores, with their tubular hollows filled with medicines.

BRIEF DESCRIPTION OF THE DRAWING

The drawing shows the cross-sectional view of a sustained release pharmaceutical plaster representing a preferable embodiment of this invention. More particularly, it is a cross-sectional drawing of a sustained release pharmaceutical plaster which mainly comprises an adhesive compound layer and a supporter which supports the adhesive compound layer which contains hollow fibers having pores opened radially through the fiber wall and having their tubular hollows filled with medicines, with empty spaces formed around the hollow fibers.

The drawing shows the supporter 1, the adhesive compound layer 2, the hollow fibers (knit) 3, the void space 4 formed around the hollow fibers, and the release sheet 5.

BEST MODE OF CARRYING OUT THE INVENTION

It is essential for the hollow fibers used in this invention to have radially opened pores. What is referred to as hollow fibers having radially opened pores here should desirably be such hollow fibers as those which have micropores scattered along the whole lengthwise profile and arranged to extend radially, and part of them, at least, are made to open into the fibers' tubular hollows.

With regard to the cross-sectional view of the hollow fibers to be used in the present invention, no restriction is laid on their external form and the internal form. For instance, both the external and the internal may take almost circular form; any one of the external and the internal may take almost circular form and the other a modified cross-sectional form; or both the external and the internal may take a modified cross-sectional form either similar or dissimilar to each other. Also no limit is set on the size of the external.

The hollow ratio of the hollow fibers of this invention may be subject to no restriction; however, it is especially desirable to keep the ratio higher than 5%. The ratio of the radial open pores to the cross-sectional area of the fiber should preferably be in the range of 0.001 to 70%, more preferably from 0.01 to 50%, still more preferably from 1 to 50% of the cross-sectional area of the fiber except for the hollow part.

As for the hollow fibers to be used in this invention, it is advisable to use the hollow fiber whose length is more than 10 times the diameter of the fiber. In case where the length is more than 10 times the diameter, the medicine filled in the tubular hollow is released much more through the radial open pores than from the cross-sectional openings of the fiber, thus increasing the sustained release effect of the medicine desirably. Also in case where the ratio of length to diameter is 10:1 or more, the plaster gives less stingy irritation to the skin of the human body upon its application to the satisfaction of the patient.

In the present invention it is advisable to use the the hollow fiber in the state of being almost infinitely long in contrast to its diameter and also in the textural form of a woven, knitted, or nonwoven fabric, because it comes to bear good handling in such a textural structure, thus producing an excellent feeling to the skin and an outstanding effect of sustained release of medicine. Of these textural forms, the knitted fabric is especially preferable since the knitted fabric has excellent elasticity and according produces the least feeling of physical unbelongingness upon application to the human skin after it is made into a pharmaceutical ceutical plaster. Knitted fabric having a unit weight of 5 to 200 g/m$^2$ especially of 10 to 100 g/m$^2$, is preferably used.

As the material of the hollow fibers to be used in this invention, selections may be made from among such polyesters as polyethylene terephthalate; such polyolefins as polyethylene and polypropylene; such polyamides as nylon 6 and nylon 66; polyurethane, cellulose acetate, polyacrylonitrile, polyvinyl chloride, and polyvinyl acetate. Of these mentioned above, polyesters are desirable, especially polyethylene terephthalate is highly desirable because of its excellent thermal stability, chemical stability, low interaction with medicines. and pharmaceutical safety.

The hollow fibers to be used in this invention can be manufactured according to such methods as described in Japanese Patent Laid-Open Publication Nos. 20612/'81, 20613/'81, and 43420/'81.

In this invention, the hollow fibers, which have radial open pores and whose tubular hollows are filled with medicines as described in the above, are used. The medicines may be contained alone in the tubular hollow, or may be made to coexist together with an adhesive compound mentioned later, or may be made to coexist together with any publicly known excipient, solubilizer, dispersing agent, and absorbefacient. The medicines may be filled into the tubular hollow of a hollow fiber by any known method. For instance, a method in which the hollow fibers are immersed in a solution in which the medicines are dissolved, and taken out of the solution, followed by the removal of the solvent; a method in which the medicines are dissolved in a solution of adhesive compound and the hollow fibers are then immersed in the solution; or a method in which the medicines are mixed with an excipient, solubilizer, dispersing agent, or absorbefacient, then the mixture is made into a solution or a paste, and the hollow fibers are immersed in the solution or smeared with the paste, may be adopted. Such procedures as heating, application of pressure, pressure reduction, and ultrasonic vibration may also be adopted.

Examples of the medicines to be used in this invention are as follows.

(1) Vasodilators for coronary vessel such as nitroglycerin, 1,2,3-propanetriolmononitrate, 1,2,3-propanetrioldinitrate, and their ester derivatives, isosorbide dinitrate, isosorbide- 5-mononitrate, pentaerythritol tetranitrate, papaverine hydrochloride, hepronicate, molsidomine, nicomol, simfibrate, verapamil, diltiazem hydrochloride, cinnarizine, dipyridamole, clonidine, nifedipine, nicardipine, trimetazidine hydrochloride, carbocromene, prenylamine lactate, dilazep dihydrochloride, and trapidil;

(2) Antiarrhythmic agent or stenocardia drugs such as pindolol, disopyramide, bupranolol hydrochloride, trichlormethiazide, furosemide, prazosin hydrochloride, metoprolol tartrate, carteolol hydrochloride, oxprenolol hydrochloride, and propranolol hydrochloride;

(3) Antihypertensive agents such as prazosin hydrochloride, ecarazine hydrochloride, and hydrolazine hydrochloride;

(4) Cardiotonics such as metildigoxin, caffeine and sodium benzoate, caffeine, dopamine hydrochloride, dobutamine hydrochloride, octopamine hydrochloride, diprophylline, ubidecarenon, oxprenolol hydrochloride, digitalein, and digoxin;

(5) Drugs for bronchial asthma such as procaterol hydrochloride, pirbuterol hydrochloride, clofedanol hydrochloride, salbutamol sulfate, propranolol hydrochloride, trimetoquinol hydrochloride, bitolterol mesilate, pindolol, isoproterenol, isoaminil citrate, carbocisteine, cephradine, tranilast, theophylline, and clenbuterol hydrochloride;

(6) Antiphlogistics and dermatological agents such as aspirin, salicylic acid, methyl salicylate, ethyl salicylate, choline salicylate, sodium salicylate, salicylosalicylic acid, salicylamide, glycol salicylate,l-menthol, aminopyrine, antipyrine, clofezone, ketophenylbutazone, camphor, mentha oil, thymol, isopropylantipyrine, phenylbutazone, feprazone, bezyl nicotimate ester, capsicum extract, capsaicin, acetaminophen, oxyphenbutazone, pentazocine, eptazocine, diffunisal, phenazole, mepirizole, piroxicam, benzydamine, phenacetin, tiaramide, bufexamac, flufenamic acid, aluminum flufenamate, indometacin, tramadol hydrochloride, ibuprofen, acemetacin, sulpyrine, guaiazulene, ketoprofen, flurbiprofen, diclofenac sodium, fenoprofen, naproxen, clidanac, sulindac, benoxabrofen, indoprofen, mefenamic acid, tolmetin, metiazinic acid, protizinic acid, perixazole citrate, pranoprofen, feprazone, phenylbutazone, fenbufen, fentizac, diaprofenic acid, tinoridine hydrochloride, zomepirac, pimeprofen, bendazac, fenoprofen calcium, prednisolone, mylproin and alclofenac;

(7) Local anesthetics such as lidocaine, benzocaine, ethyl aminobenzoate, procaine hydrochloride, dibucaine, and procaine;

(8) Diuretics such as mefruside, penflutizide, bumetanide, hydrothiazide, bentroflumethiazide, and reserpine;

(9) Hypnotics and sedatives such as methaqualone, glutethimide, flurazepam, bromovalerylurea, flurazepam hydrochloride, nitrazepam, haloxazolam, triazolam, phenobarbital, chloral hydrate, nimetazepam, and estazolam;

(10) Central nervous system agents such as levodopa, fluphenazine, flutazolam, phenobarbital, phenobarbital sodium, methylphenobarbital, thioridazine, diazepam, benzbromarone, reserpine, sulpiride, alprazolam, clocapramine hydrochloride, clotiazepam, chlorpromazine, haloperidol, nitrazepam, and lithium carbonate;

(11) Adrenocortical hormones such as cortisone acetate, hydrocortisone acetate, hydrocortisone, prednisolone, sodium hydrocortisone succinate, triamcinolone acetonide, triamcinolone diacetate, dexamethasone phosphoric ester, methylpredonisolone, dichlorisone acetate, methylpredonisolone acetate, fluocinolone acetonide, dexamethasone acetate, and dexamethasone;

(12) Antitubercular agents such as sulfa drugs like sulfadimethoxine, sulfisoxazole, and sulfisomidine; ethambutor hydrochloride, isoniazid, and calcium paraaminosalicylate;

(13) Antihistamic and antiallergic agents such as homochlorcyclizine hydrochloride, diphenhydramine hydrochloride, chlorpheniramine, diphenylimidazole, chloropheniramine maleate, glycyrrhetic acid, tranilast, and ketotifen;

(14) Drugs for myasthenia such as pyridostigmine bromide;

(15) Drugs for post-cerebral embolism such as ifenprodil tartrate;

(16) Antibiotic drugs such as penicillin, tetracycline, oxytetracycline, chlortetracycline, chloramphenicol, sulfonamide, talampicillin hydrochloride, fradiomycin sulfate, erythromycin, tetracycline hydrochloride, bacampiciline hydrochloride, fradiomycin, leucomycin, cefraxadine, cephalosporin, ampicillin, and cefalexin;

(17) Antibacterial and antifungal agents such as iodine, povidone iodine, boric acid, sodium borate, oxydol, potassium permanganate, ethanol, isopropanol, formalin, cresol, dimazole dihydrochloride, siccanin, phenyliodoundecynoate, hexachlorophene, creosote, resorcin, acrinol, methylrosanilinium chloride, benzethonium chloride, sodium lauryl sulfate, mercuric chloride, and meclosorb;

(18) Keratolytics such as pine tar and chrysarobin;

(19) Antiepileptics such as primidone, valproate sodium, nitrazepam, meprobamate, and clonazepam;

(20) Antineoplastic agents such as bleomycin, aclacinomycin, adriamycin, carmofur, pipobroman, melphalan, carboquone, thioinosine, tamoxifen citrate, peplomycin, tegafur, 5-fluorouracil and its derivatives, and mitomycin;

(21) Sex hormones such as progesterone, hydroxyprogesterone caproate, hydroxyprogesterone acetate, testosterone enanthate, and chlormadinone acetate;

(22) Vitamins such as pyridoxine hydrochloride, cobamamide, nicotinamide, pantethein, calcium pantothenate, flavin adenine dinucleotide, folic acid, pyridoxal phosphate, ascorbic acid, vitamin A, vitamin $D_3$, vitamin E, ergocalciferol, $1\alpha$-hydroxy vitamin $D_3$, $1\alpha,25$-dihydroxy vitamin $D_3$, $1\alpha, 24$-dihydroxy vitamin $D_3$, octapanin hydrochloride, riboflavin, and riboflavin tetrabutyrate;

(23) Antitussives and expectorants such as beclometasone propionate, hexoprenaline sulfate, salbutamol sulfate, powdered opium, ethylmorphine hydrochloride, morphine hydrochloride, and opium alkaloids hydrochloride;

(24) Drugs for diabetes mellitus such as glibenclamid and glymidine sodium;

(25) Drugs for constipation such as picosulfate sodium, dantrolene sodium, sennoside A.B calcium salt, and cascara sagrada liquid extract;

(26) Immuno modulators such as D-penicillamine, bestatin, levamisole and carfecillinsodium;

(27) Drugs for cystitis, chronic cystitis, and urethritis such as carindacillin sodium, sodium pivmecillinam hydrochloride, cefroxadine, carfecillin sodium, cefaclor, enoxacin, cefadroxil, hexamine mandelate, and sulfamethizole;

(28) Ophthalmic remedies such as catalin;

(29) Antiulcer agents such as aceglutamide aluminum, cetraxate hydrochloride, pirenzepine hydrochloride, cimetidine, L-glutamine, and gefarnate;

(30) Drugs for arterial disorder such as clinofibrate, elastase, simfibrate, bencyclane fumarate, and niceritrol;

(31) Drugs for suppurative diseases such as sulfisomidine sodium, sulfamethoxazole sodium, sulfadiazine silver, gentamicin sulfate, and mafenide acetate;

(32) Drugs for parasitic cutaneous diseases such as clotrimazole, siccanin, exalamide, and pimaricin.

These medicines mentioned above are used singly or as a mixture of more than one properly chosen.

As the medicines to be used in this invention, vasodilators for coronary vessel, antiarrhythmic agents, stenocardia drugs, cardiotonics, and antihypertensive agents are very desirable and the vasodilators for coronary vessel are especially desirable. The amounts of the drugs to be used may be properly decided depending upon the pharmacological potency and the absorptivity to the skin of the drug.

The plaster of this invention has hollow fibers, whose tubular hollows are filled with medicines chosen from those mentioned above, laid inside the adhesive compound layer. The term "inside the adhesive compound layer" used here does not mean the outer surface of the adhesive compound layer which directly come into contact with the skin upon which it is applied but means the inner part of the adhesive compound layer. In this invention, it is advisable to place the hollow fibers in the central part of the adhesive compound layer. With the hollow fibers placed in the central part of the adhesive compound layer, such side effects as contact-type dermatitis may be suppressed and the plaster comes to display an excellent sustained release effect of medicines.

As the adhesive material to be used for the making of the adhesive compound layer in this invention, ordinary pressure sensitive adhesives are used and may be chosen, for instance, from acrylic resins; viscous rubber compounds mainly composed of silicone rubber, polyisoprene rubber, styrene-butadiene rubber, acrylic rubber, and natural rubber; viscous vinyl compounds such as polyvinyl alcohol and ethylene-vinyl alcohol copolymer; and viscous compounds such as silicone adhesives, polyurethane elastic body, polyester elastic body, and polybutadiene elastic body. Among these adhesive compounds mentioned above, acrylic resins are desirable, and acrylic resins, which are obtained by copolymerization of (1) at least 50 to 98 mole % of (meth)acrylic alkyl ester having an alkyl group of carbon number of 4 or more and (2) 2 to 50 mole % of acrylic acid or/and methacrylic acid, are especially desirable. Examples of (meth)acrylic alkyl ester having an alkyl group of carbon number of 4 or more include butyl (meth)acrylate, amyl (meth)acrylate, hexyl (meth)acrylate, keptyl (meth)acrylate, octyl (meth)acrylate, nonyl (meth)acrylate, decyl (meth)acrylate, and 2-ethylhexyl (meth)acrylate. These adhesives may be used singly or as a complex adhesive of more than one.

In this invention, the adhesive compound layer made of the aforementioned adhesives may also be allowed to contain medicines besides making the hollow fibers contain medicines in their tubular hollows.

It is usually preferable to make the adhesive compound layer ranging from 5 to 1,000$\mu$ in thickness, more preferably from 10 to 500$\mu$.

In this invention, void spaces are provided around the hollow fibers, whose tubular hollows are filled with medicine placed inside the adhesive compound layer as explained hereinbefore, so that the medicines can be supplied in a desirable way of sustained release with no holding off to give a high efficiency in the small surface area of a plaster, and moreover the sweaty stuffiness and contact-type dermatitis can be remarkably controlled, thus solving the problems that have not been unlocked by the conventional plasters.

It is desirable to provide such void spaces around the hollow fibers in such a way as to make 10% to 95%, preferably 50 to 95%, of the total surface area of all the filaments, which constitute the hollow fibers, left free from being adhered to the adhesive compound layer.

If the unadhered area is less than 10% of said total surface area, it becomes difficult to secure enough void space, thus making it difficult for the plaster to control the release of medicines. If the unadhered area exceeds 95% of the total surface area, it is difficult for the plaster to maintain its set form.

To establish the aforementioned void spaces around the hollow fibers efficiently, it is advisable to use the hollow fibers in the textural form of a woven, knitted, or nonwoven fabric, which is then placed and pressed between the upper part and the lower part of the adhesive compound layer, thus forming a void space with ease and convenience.

In case where void spaces are established around the hollow fibers, it is desirable to use medicines which display good evaporativity when applied to the human body.

As the medicines which display good evaporativity upon application to the human body, such solid ones that volatilize by sublimation or liquid ones that evaporate may be used. As the examples of such medicines, nitric esters such as isosorbide dinitrate and nitroglycerin may be mentioned as typical ones. Guaiazulene, halomethane, chloral hydrate, menthol, clenbuterol hydrochloride, camphor, such salicyclic ester as methyl salicylate and monoglycolate salicylate, and such vitamin $D_3$ derivatives as 1$\alpha$-hydroxy vitamin $D_3$, 1$\alpha$,25-dihydroxy vitamin $D_3$, and 1$\alpha$,24-dihydroxy vitamin $D_3$ may also be mentioned.

It has been made possible for the plaster to continue the supply of medicines almost at a constant rate smoothly by the establishment of void spaces around the hollow fibers and by use of medicines which display evaporativity when applied to the human body.

The reason for this fact may be explained on a reasonable assumption that medicines evaporated from the surfaces of hollow fibers are difused more mildly and that at a constant rate when the medicines in vaporphase are absorbed and difused into the adhesive compound layer which has a wide surface facing to the void spaces as composed with the case where the medicines coming out of the hollow fibers directly diffuse into the adhesive compound layer without evaporating substantially.

Though it is not yet fully clarified why a plaster provided with void spaces can effectively minimize the sweaty stuffiness and contact-type dermatitis in spite of the fact that the void spaces do not open directly to the skin, it is assumed that the extremely improved pliability of the plaster due to the formation of void spaces around the hollow fibers materially reduce the physical stimulation when it is applied to the skin.

Generally speaking, when a plaster comes in contact with moisture, the sweaty stuffiness and contact dermatitis tend to be caused readily; however, it may be assumed that the plaster of this invention, upon coming in contact with moisture, make the moisture, which passes from the skin through the adhesive compound layer up to the hollow fibers, flow through the void spaces and go out from their ends opening at the borders of the plaster, thus causing less sweaty stuffiness and contact dermatitis than a plaster in which absorbed moisture is discharged through the supporter as described later.

As excellent sustained release pharmaceutical plaster having void spaces around the hollow fibers prepared according to this invention as described above will further be explained referring to its drawing. The drawing shows the cross-sectional view of a sustained release pharmaceutical plaster having void spaces around the knitted fabric made to hollow fibers produced according to this invention. In the drawing, the numeral 1 indicates the supporter, 2 the adhesive compound layer, 3 the hollow fibers, 4th void space, and 5th release sheet. As shown in the drawing, the void space around the hollow fibers are formed by leaving part of the surface of a single yarn of the hollow fibers not adhered to the adhesive compound layer. In the hollow fibers, interspaces between the fiber bundles may be made to communicate to each other or may be filled with the adhesive compound layer.

With regard to the plaster of this invention, it is advisable to make the total residual amount of the solvent used in the production of the plaster less than 50 ppm of the weight of the adhesive compound layer including the hollow fibers. The side effects such as contact dermatitis can be controlled by keeping the residual solvent below 50 ppm.

As the examples of solvents that are usually used in preparing an adhesive compound layer, ethyl acetate, propyl acetate, butyl acetate, aceton, methyl ethyl ketone, methyl isobutyl ketone, toluene, xylene, methanol, ethanol, isopropanol, butanol, methylene chloride, chloroform, carbon tetrachloride, and diethyl ether may be mentioned.

The plaster of this invention is equiped with a supporter to support the adhesive compound layer. The supporter should desirably satisfy the requirements that it does not hinder the medicines contained in the adhesive compound layer from mobilizing, that it does not decrease the adhesiveness of the adhesive compound layer to the skin, and that it does not give a feeling of physical disorder to the skin upon its application. Such polyolefins such as polyethylene and polypropylene, such polyesters as polyethylene terephthalate, such polyamides as nylon 6 and nylon 66, polyvinyl alcohol, vinylidene chloride, polyurethane, ethylene-vinyl acetate copolymer, metal leaf, rubber sheet, film, woven fabric, knitted fabric, nonwoven fabric, and foil may be used for the supporter. The supporter made of these materials may be used singly, as a composite or a laminate.

Of these supporter materials, a supporter made of polyester, especially polyethylene terephthalate, is good from the viewpoints of productivity of the plaster, release of medicines from the plaster, stability, and prevention of contact dermatitis.

For the plaster of this invention, it is desirable to use a film ranging from 4.9 to $0.9\mu$ in thickness as the supporter.

When the thickness exceeds $4.9\mu$, the plaster comes to lose in pliability and make the contact dermatitis more serious. The release of medicines from the plaster also becomes irregular.

When the thickness is less than $0.5\mu$, the supporting film is apt to break even by a small external force when caught by the clothes, nails, and other abrasive materials, thus degrading the stability of the plaster. Furthermore, while the plaster is in storage or in application, the medicines escape through the thin film, thus expediting the loss of stability with the passage of time.

In embodying the present invention, a high polymer layer made of an ethylene-vinyl acetate copolymer or polyvinyl acetate may be established between the supporter and the adhesive compound layer, if necessary.

In the present invention, a colored adhesive layer containing such a coloring agent as Yellow No. 4 may be placed between the supporter and the adhesive compound layer or laid in the laminated supporter in case where the medicines having poor light stability like nifedipine are to be used.

In the present invention, a release sheet may be provided on the adhesive compound layer. A release sheet may be of any type ordinarily used such as coated paper or film.

A sustained release pharmaceutical plaster of this invention can be produced according to the following method.

The method of the production comprises spreading and sticking fast an adhesive compound layer onto the supporter; placing hollow fibers, provided with radially open micropores and have their tubular hollows filled with medicines, on the adhesive compound layer; and further laminating another adhesive compound layer thereon.

The spreading and sticking fast the adhesive compond layer onto the supporter can be effected by coating the supporter with a solution of adhesive compound or by laminating the supporter with an adhesive compound layer prepared separately beforehand. The laminating of the hollow fibers and the succeeding lamination of the adhesive compound layer can be carried out by firstly laying the hollow fiber and then applying an adhesive compound solution thereto, or by placing an adhesive compound layer prepared beforehand or an adhesive compound layer which is already stuck to a release sheet or film on the already laid hollow fibers, followed by adhereing them together under proper pressure.

In the present invention, the hollow fibers are used in the structural form of a woven, knitted, or nonwoven fabric and the hollow fibers are placed on an adhesive compound layer having a proper viscosity spread on a supporter, and a succeeding secondary adhesive compound layer is placed thereon, and the file of these layers is then laminated together under proper pressure, and heating if desired, to produce a plaster which has void spaces around the hollow fibers as described in the above.

The plaster of this invention can also be produced by first establishing an adhesive compound layer respectively on both surfaces of hollow fibers having radially open micropores and being filled with medicines and then laminating the adhesive compound layer with a supporter. In this case, a plaster having void spaces around the hollow fibers can be obtained by laminating hollow fibers in the form of a woven, knitted, or nonwoven fabric and adhesive compound layers having a proper viscosity under proper pressure.

The plaster of this invention can also be produced by placing hollow fibers with their tubular hollows filled with medicines on the supporter and then applying an adhesive compound solution thereto.

As described before, it is desirable in this invention to keep the residual amount of the solvent in the adhesive compound layer, inclusive of the hollow fibers, of the plaster below 50 ppm so that the side effects such as sweaty stuffiness and contact dermatitis may be suppressed. It is, therefore, desirable to decrease the amount of the solvent remaining in the adhesive compound layer or the hollow fibers by subjecting the plaster to heat treatment.

In case where the plaster is produced, with use of hollow fibers which are made to contain medicines and the adhesive compound layer which is prepared separately, by laminating said hollow fibers filled with medicines, adhesive compound layer, and supporter, the adhesive compound layer can stand against enough heating to remove the solvent even if the medicines have not enough heat stability.

The plaster of this invention may contain an absorption promoter, solubilizing agent, diffusion promotor, and filling material As the absorption promotor or diffusion promotor, such surfactants as sodium lauryl sulfate, sodium dodecylbenzenesulfonate, alkyldiphenyl ether sodium disulfonate, dioctylsulfosuccinate, and polyoxyalkylphenyl ether sulfate ammonium salt; such alcohols as ethanol, glycerin, diethylene glycol, propylene glycol, polyethylene glycol, and higher fatty acid alcohol; dimethyl sulfoxide and alkylmethyl derivatives; salicyclic acid, urea, dimethylacetamide, dioctyl sebacate, lanolin, allantoin, squalene, carbopol, diisopropyl adipate, pyroglutamic acid lauryl ester, ethyl laurate, methyl nicotinate, sorbitol, and pyrrohidone derivatives such as dodecylpyrrolidone and methylpyrrolidone, olive oil, castor oil, liquid paraffin, vaseline, gelatin, amino acid, benzyl nicotinate, l-menthol, camphor, and dodecylazacyclohepthane-2-one may be used.

As the solubilizing agent, there are, for instance, benzyl alcohol, butyl benzoate, isopropyl myristicic acid, octanol, 1,3-butanediol, crotamiton, and polypropylene glycol.

As the filling material, water, titanium oxide, calcium carbonate, carbon black, red iron oxide, dyes and pigments, liquid paraffin, vaseline, lactose, perfume, deodorant, powders or moldings of synthetic resin such as polyethylene, polypropylene, polyester, and polystyrene may be mentioned.

The invention will be further illustrated by the following examples. All parts in the Examples and Reference Examples are by weight.

REFERENCE EXAMPLE 1

Production of Hollow Fibers (1) Hollow fiber specimen (1)

297 parts of dimethyl terephthalate, 265 parts of ethylene glycol, 53 parts of 3,5-di(carbomethoxy)sodium benzenesulfonate (11.7 mole % to dimethyl terephthalate), 0.084 parts of manganese acetate tetrahydrate, and 1.22 parts of sodium acetate trihydrate were placed in a glass flask equipped with a rectification column and subjected to the ester interchange reaction according to an ordinary method. After the theoretical amount of methanol was distilled away, the reaction product was put in a polycondensation flask equipped with a rectification column together with 0.090 part of 56% phosphoric acid aqueous solution as the stabilizer and 0.135 part of antimony trioxide as the catalyst. The reaction was carried out at 275° C. for 20 minutes at ordinary pressure, then 15 minutes at 30 mmHg to give a copolymer having a limiting viscosity number of 0.405 and a softening point of 200° C. After the reaction was over, the obtained copolymer was formed into chips according to the generally practised method.

15 parts of thus obtained copolymer chips and 85 parts of polyethylene terephthalate chips having a limiting viscosity number of 0.640 were mixed for 5 minutes in a NAUTA mixer (Hosokawa Iron Works) and were then dried in the stream of nitrogen at 110° C. for 2 hours and further at 150° C. for 7 hours. Thereafter, the mixed chips were melt-kneaded at 290° C. by use of a double screw extruder to give chips. The chips had a limiting viscosity number of 0.520 and a softening point of 262° C.

After thus prepared chips were dried according to the ordinary method, they were spun by use of a spinneret with circular slits, each having a width of 0.05 mm and a diameter of 0.6 mm, which were closed at two points to form circular arc openings, according to an ordinary method to give hollow fibers (void ratio 25%) having a ratio of 2:1 between the outside diameter and the inside diameter. Thus obtained raw fibers were 300 denier/24 filaments. These raw fibers were drawn by a drawing factor of 4.2 according to the ordinary method to obtain multifilament yarns of 71 denier/24 filaments. A knitted fabric was made of these multifilament yarns and was scoured according to the ordinary procedure, dried, and treated in 1% caustic soda aqueous solution at a boiling temperature for 2 hours to obtain a fabric having an alkaline cleaning loss in weight of 15%, water absorption rate of 3 seconds, water absorption degree of 80%, and unit weight of 38 g/cm².

The water absorption rate and the water absorption degree were determined by the methods mentioned below.

(a) Water Absorption Rate Test Method (based on JIS-L1018)

The fibers were made into a fabric, which was then washed 10 times according to the schedule with an aqueous solution of 0.3% anionic detergent Zabu (Kao Soap Co., Ltd.) in a home electric washing machine at 40° C. for 30 minutes each time. The specimen was then dried and strentched horizontally on a frame. A drop of water (0.04 cc) was let fall from a height of 1cm on the specimen and the time required for the waterdrop to be completely absorbed by the specimen and no reflected light was observed any longer.

(b) Water Absorption Degree Determination Method

Specimens obtained from the dried fabric were immersed in water for 30 minutes or more and then dehydrated for 5 minutes in the hydroextractor attached to a home electric washing machine. The water absorption degree was calculated from the weight of the dry specimen and the weight of the specimen after dehydration by the following formula:

$$\text{Water absorption degree} = \frac{\left(\begin{array}{c}\text{weight of the}\\\text{specimen after}\\\text{dehydration}\end{array}\right) - \left(\begin{array}{c}\text{weight of}\\\text{the dry}\\\text{specimen}\end{array}\right)}{(\text{Weight of the dry specimen})} (\%)$$

The hollow fibers obtained by the aforementioned method were ones dotted with micropores extending radially on the cross section and being arranged all along the length of the fibers and at least part of the micropores were open through the fiber walls to the tubular hollow.

(2) Hollow Fiber Specimen (2)

This is a specimen obtained from the same knitted fabric as prepared in the hollow fiber specimen (1) without subjecting it to the alkaline treatment. It is a knitted fabric having the water absorption rate of 230 seconds and the water absorption degree of 38%.

The hollow fibers of this fabric have no radially extending open micropores.

REFERENCE EXAMPLE 2

Preparation of adhesive compound solution and adhesive compound layer

A reaction vessel equipped with a reflux condenser and an agitator was fed with 97.4 parts of 2-ethylhexyl acrylate, 2.5 parts of methacrylic acid, 0.1 part of polyethylene glycol (polymerization degree 14) dimethacrylate, 1.0 part of benzoyl peroxide, and 100 parts of ethyl acetate and the polymerization was carried on in the atmosphere of nitrogen at 60° for 9 hours with slow stirring. The polymerization conversion rate was 99.8%.

Addition of 500 parts of ethyl acetate to the obtained polymeric solution gave an adhesive compound solution was its solid substance concentration adjusted to about 20%. The ethyl acetate solution containing said adhesive compound was spread on a release paper coated with silicone in such a way as to give it a thickness of 20μ when dried, and it was dried at 90° C. for 10 minutes to form an adhesive compound layer.

EXAMPLE 1

After 10 parts of the hollow fiber specimen (1) was immersed for 1 minute in 100 parts of an acetone solution containing 50 parts of isosorbide dinitrate kept in a vessel, the hollow fiber specimen (1) was taken out and air-dried.

This hollow fiber specimen containing isosorbide dinitrate was placed on a $5\mu$ thick supporter made of polyethylene terephthalate, upon which an adhesive compound solution comprising 100 parts of solid substances in the adhesive compound solution and 5 parts of isosorbide dinitrate was coated in such a way as to make a thickness of $200\mu$ upon drying and to deep the isosorbide dinitrate-containing hollow fiber specimen midmost the adhesive compound layer, thus obtaining a plaster which contained 15 $g/m^2$ isosorbide dinitrate.

EXAMPLE 2

The hollow fiber specimen (1) was left immersed in an adhesive compound solution, comprising 100 parts of solid substance of the adhesive compound solution and 20 parts of isosorbide dinitrate, with stirring under reduced pressure overnight. Then the hollow fiber specimen (1) was taken out, made to pass through ethyl aetate within 1 second, and dried at 60° C. for 2 hours. The hollow fiber specimen containing the adhesive compound and medicines were again subjected to the aforementioned treatment to give the hollow fiber specimen filled with an adhesive compound containing isosorbide dinitrate. This hollow fiber specimen was placed on a supporter made of polyethylene terephthalate and then subjected to the same procedure as Example 1 to obtain a plaster.

COMPARISON EXAMPLE 1

A plaster having an adhesive compound layer, $200\mu$ in thickness, containing isosorbide dinitrate, was obtained according to Example 1, except for the use of the hollow fiber specimen (2) instead of the hollow fiber specimen (1). The content of isosorbide dinitrate was 8 $g/m^2$.

COMPARISON EXAMPLE 2

A plaster having an adhesive compound layer, $200\mu$ in thickness, containing isosorbide dinitrate, was obtained according to Example 2, except for use of the hollow fiber specimen (2) instead of the hollow fiber specimen (1).

EXPERIMENT EXAMPLE 1

A piece, 2 cm×4 cm, was cut from the plaster obtained in Example 1 and a piece, 3 cm×5 cm, was cut from the plaster obtained in Comparison Example 1, so that the contents of isosorbide dinitrate of the two test pieces were made equal to each other. The two test pieces were respectively applied to the depilated backs of rabbits weighing about 2.8 kg. The blood was drawn from the rabbits at intervals of prescribed time to determine the blood concentration.

The blood concentration of isosobide dinitrate was determined by the method mentioned below.

The blood plasma, which had been separated from 3 ml of the respectively collected blood, was extracted with 4 ml of n-hexane. The hexane hexane layer was condensed to nearly dryness, and then made to be 110 $\mu l$ by adding ethyl acetate. The determination was conducted by GC-ECD. The result is shown in Table 1.

TABLE 1

| Blood concentration of isosorbide dinitrate in rabbits (Unit: ng/ml) | | | | | | |
|---|---|---|---|---|---|---|
| | Time of application (hour) | | | | | |
| Plaster | 1 | 3 | 6 | 12 | 24 | 48 |
| Plaster obtained in Example 1 | 4.2 | 5.1 | 4.7 | 4.8 | 4.1 | 3.9 |
| Plaster obtained in Comparison Example 1 | 5.4 | 9.3 | 8.2 | 6.0 | 2.1 | 1.3 |

As apparent from Table 1, it has been found that the plaster prepared by use of sepcifically treated hollow fibers of this invention has an excellently sustained release of medicines.

EXAMPLE 3

After the hollow fiber specimen (1) was immerced in an adhesive compound solution, which contained 20 parts of nifedipine to 100 parts of the solid substance contained in the adhesive compound solution, left overnight with stirring under reduced pressure, then taken out of the solution, and made to pass through ethyl acetate within 1 second, the hollow fiber specimen (1) was dried at 40° C. for 6 hours. The hollow fiber specimen which contained nifedipine and adhesive compound was again subjected to the aforementioned procedure to give the hollow fiber specimen filled with the adhesive compound containing nifedipine.

Apart from the above, an adhesive compound solution, which contained 5 parts of yellow No. 5, Japanese Pharmacopoeia (sunset yellow FCF) to 100 parts of solid substance in the adhesive compound solution, was applied to one side of a $5\mu$ thick polyethylene terephthalate film, and was dried at 60° C. for 2 hours to form a $100\mu$ thick adhesive compound layer which contained a coloring material. As the backing material, a $5\mu$ thick polyethylene terephthalate film was applied thereto under pressure to make a supporter.

The hollow fiber specimen filled with an adhesive compound containing nifedipine was placed on the abovementioned supporter, and an adhesive compound solution containing 10 parts of nifedipine to 100 parts of solid substance was applied thereto and was dried at 40° C. for 6 hours to form an adhesive compound layer, about $200\mu$ in thickness, holding the hollow fiber specimen buried approximately midmost the adhesive compound layer.

Thus prepared plaster was cut into 2 cm×4 cm pieces, and were applied to the depilated backs of rabbits. The residual nifedipine in the plaster 12 hours and 24 hours after the application was determined by the gas chromatography with the results of 76% and 53% respectively.

When other 2 cm×4 cm pieces of the same plaster were covered with a release sheet respectively and left for 24 hours exposed to the light in the room, they showed residual nifedipine of 99.7%.

EXAMPLE 4

8 parts of the hollow fiber specimen (1) were put in the vessel which contained 100 parts of an acetone solution inclusive of 40 parts of isosorbide dinitrate for 1 minute. Then the specimen was taken out of the vessel and air dried. One part of this hollow fiber specimen contained about 0.1 part of isosorbide dinitrate.

An adhesive compound solution obtained in Reference Example 2 was applied to a $5\mu$ thick polyethylene terephthalate film used as a support in such an amount as to make a dry thickness of 60μ and was dried at 90° C. for 10 minutes. The aforementioned hollow fiber specimen which contained isosorbide dinitrate was placed on the said adhesive compound layer and an adhesive compound layer obtained in Reference Example 2 was laid on the hollow fiber specimen to obtain a plaster which had the hollow fiber specimen in the middle of the adhesive compound layer. The content of isosorbide dinitrate in the plaster was 10 g/m². When the cross section of this plaster was observed through a magnifier, it was found that about 80% of the total surface area of its filament yarn did not directly contact the adhesive compound layer and that there were many void spaces around the hollow fiber structure. This plaster is referred to as plaster A.

Separately another type of plaster was prepared by placing the adhesive compound layer obtained in Reference Example 2 on the hollow fiber specimen containing isosorbide dinitrate spread on the 60μ thick adhesive compound layer obtained according to the same method mentioned above while applying a heavy pressure on both ends so that no air might be involved inside with the hollow fiber specimen held in the middle of the adhesive compound layer. The whole plaster contained isosorbide dinitrate at a ratio of 10 g/m². When the cross section of this plaster was observed through a magnifier, no void space was detected around the hollow fiber structure. This plaster is referred to as plaster B.

This plaster was cut into several pieces of 2 cm×2 cm, which were then applied to the depilated backs of rabbits weighing about 2.7 kg. The blood was collected from the rabbits at prescribed times to determine the blood concentration.

TABLE 2

| Blood concentration of isosorbide dinitrate in rabbits (Average of 5-rabbit groups) (ng/ml) | | | | | | |
|---|---|---|---|---|---|---|
| | Time of application (hour) | | | | | |
| Plaster | 1 | 3 | 6 | 12 | 24 | 48 |
| Plaster A | 0.9 | 2.5 | 2.6 | 2.8 | 2.5 | 1.6 |
| Plaster B | 1.3 | 3.9 | 4.2 | 2.9 | 0.7 | 0.2 |

As clearly seen from Table 2, plaster A and plaster B are both excellent in their sustained rease of medicines; however, plaster A which had void spaces around the hollow fibers has an extremely excellent sustained release effect.

EXPERIMENT EXAMPLE 2

To evaluate the plaster of this invention from the viewpoint of its stuffy feeling only, the test was made by use of a plaster containing no medicines. A sample, which corresponds to a so-called placebo according to Example 4 with ommission of the process where the hollow fiber specimen was made to contain isosorbide dinitrate, was prepared. As the result of an investigation made on the sample which had void spaces around the hollow fibers in cross sectional view of the plaster, it was found that the plaster caused no stuffy feeling and gave no urtication to the skin.

EXAMPLE 5

After 10 parts of hollow fiber specimen (1) was made to absorb 10 parts of an acetone which contained 2 parts of isosorbide dinitrate, the specimen was air-dried to have acetone removed.

This hollow fiber specimen containing 10 g/m² of isosorbide dinitrate was placed between the two adhesive compound layers prepared in Reference Example 2. A 3μ thick polyethylene terephthalate film was put on one surface of the adhesive compound layer under pressure to obtain a plaster with the hollow fiber specimen sandwiched in the middle of the adhesive compound layer and about 84% of the total surface area of the filament yarn was not in direct contact with the adhesive compound layer leaving many void spaces seen around the hollow fibers.

EXAMPLE 6

10 parts of the hollow fiber specimen (1) was made to absorb 10 parts of an acetone solution containing 2 parts of isosorbide dinitrate and then air-dried to remove acetone.

This hollow fiber specimen containing isosorbide dinitrate was put between the two adhesive compound layers obtained in Reference Example 2, pressed together in such a way as not to involve air between them, and finally had a 3μ thick polyethylene terephthalate film applied to one side of the adhesive compound layer under pressure, to obtain a plaster having the hollow fiber specimen in the middle of the adhesive compound layer but having no void spaces around the hollow fibers.

COMPARISON EXAMPLE 3

After 10 parts of the hollow fiber specimen (1) was made to absorb 10 parts of an acetone solution containing 2 parts of isosorbide dinitrate, acetone was removed by air-drying.

An adhesive compound solution obtained in Reference Example 2 was applied to a 3μ thick polyethylene terephthalate film functioning as a supporter in such an amount as to make a thickness of 40μ after drying, and then the hollow fiber specimen containing isosorbide dinitrate was burried therein, to obtain a plaster provided with hollow fibers on the outer surface of the adhesive compound layer.

EXPERIMENT EXAMPLE 3

The respective plasters obtained in Examples 5 and 6 and Comparison Example 3 were cut into 2 cm×4 cm pieces, each piece containing 5 mg of isosorbide dinitrate and applied to the depilated backs of rabbits weighing about 3.1 kg. The blood was collected at scheduled time and the blood concentrations were determined. The result is shown in Table 3.

TABLE 3

| Blood concentration of isosorbide dinitrate in rabbits (unit: ng/ml) | | | | | | |
|---|---|---|---|---|---|---|
| | Time of application (hour) | | | | | |
| Plaster | 1 | 3 | 6 | 12 | 24 | 48 |
| Plaster obtained in Example 5 | 6.3 | 9.2 | 11.8 | 9.5 | 7.7 | 5.1 |
| Plaster obtained in Example 6 | 6.8 | 11.5 | 16.0 | 10.3 | 6.2 | 2.7 |
| Plaster obtained in Comparison Example 3 | 16.1 | 8.2 | 14.0 | 7.9 | — | — |

Plasters obtained in Comparison Example 3 came off from the backs of the rabbits after 12-hour application and no more data were available thereafter.

As clearly shown in Table 3, the plaster, which ahs the hollow fibers on the outer surface of the adhesive compound layer, has a poor adhesivity to the skin and its sustained release effect of medicines is also not satisfactorily enough. On the contrary, the plasters of this invention having the hollow fibers in the adhesive compound layer have an excellent adhesivity to the skin and the sustained release effect of medicines is also highly excellent.

EXPERIMENT EXAMPLE 4

The following experiment was conducted to examine the desirable thickness of the supporter.

A plaster that may be called a placebo was prepared according to Example 5, except for the nonuse of isosorbide dinitrate and the use of films mentioned in Table 4 in the place of polyethylene terephthalate film, and six pieces cut from the plaster were applied at random to the central part on the backs of three healthy adults, 20 to 30 years old, weighing 56 to 72 kg, and the contact-type dermatitis at the plaster applied sites was observed and judged when the plasters were removed two days after their application.

The judgement was based on the total scores given by three judges, who gave zero point for causing no reaction, 1 point for causing a slight red to the plaster applied site, 2 points for causing an apparent red, and 3 points for causing contact-type dermatitis including papule, etc., and the result is shown in Table 4.

TABLE 4

| | Test by application to humans | | |
|---|---|---|---|
| | Film material | Film thickness (microns) | Contact dermatitis caused to skin |
| Test 1 | Polyethylene terephthalate | 4.5 | 4 |
| Test 2 | Polyethylene terephthalate | 3.5 | 2 |
| Test 3 | Polyethylene terephthalate | 1.5 | 2 |
| Test 4 | Polyethylene terephthalate | 6 | 5 |
| Test 5 | Polyethylene terephthalate | 0.43 | 2 |
| Test 6 | Vinylidene chloride | 15 | 7 |

*Film broke 6 hours after application

As clearly seen from Table 4, the plasters whose supporters are in the range of 0.5 to 4.9 microns in thickness are especially excellent in that they scarcely cause contact dermatitis, etc.

EXPERIMENT EXAMPLE 5

The following tests were performed to examine the desirable range of the quantity of residual solvent in the adhesive compound layer inclusive of the hollow fibers.

(i) Test 1

An adhesive compound solution was applied to the surface of release paper coated with silicone in such an amount as to make a dry thickness of 30$\mu$ and was dried at 90° C. for 3 minutes and further at 110° C. for 10 minutes. The obtained adhesive compound layer was immersed in methanol to have the residual solvent removed by extraction and subjected to gas chromatography to have the amount of ethyl acetate measured, giving a result of 12 ppm.

Thus obtained adhesive compound layers were laminated on both surfaces of the hollow fiber specimen (1) not containing medicines. A 5-micron polyethylene terephthalate film was then placed on the free surface of the adhesive compound layer and pressed together to obtain a placebo plaster which did not contain medicines.

The placebo plaster was cut into 2 cm×2 cm pieces, which were then applied to the middle of backs of three healthy adults of 20 to 30 years old weighing 55 to 72 kg. To days later, the plasters were removed and the conditions of the skin at the site of application were judged. The judgement was based on the total scores of points given by three judges who gave zero point for causing no reaction, 1 point for causing a slight red to the plaster applied site, 2 points for causing an apparent red, and 3 points for causing contact-type dermatitis including papule, etc., and the result is shown Table 5.

(ii) Test 2 and Test 3

Placebo plasters were prepared according to the aforementioned Test 1, except for the change in the drying conditions and the resulting change of the residual amount of the solvents, and the tests similar to the above one were performed, with the result as shown in Table 5.

TABLE 5

| | Residual amount of ethyl acetate (ppm) | State of contact dermatitis |
|---|---|---|
| Test 1 | 15 | 3 |
| Test 2 | 46 | 4 |
| Test 3 | 72 | 6 |

As apparent from Table 5, it is desirable to adjust the residual amount of the solvent below 50 ppm.

EXPERIMENT EXAMPLE 6

To ascertain the reason for not causing sweaty stuffiness by use of the plaster of this invention, the moisture permeability of the plaster and the stability of the medicines were examined as follows.

The plaster containing 10 g/m$^2$ of isosorbide dinitrate obtained in Example 5 was cut into 7 cm×7 cm pieces of specimen plaster, which were then put on a glass sheet with their adhesive sides attached to the glass. The specimens were immersed in water for 30 seconds, and the moisture content of the whole plaster immediately after the delivery out of the immersion was determined by Karl Fischer's method after the extraction of moisture from the plaster by use of methanol, with the result of 2.1%. The content of isosorbide dinitrate was 49 mg.

Thus moisturized specimen plasters were left standing at room temperature to have the moisture content versus the isosorbide dinitrate content determined as they changed with the time passing. The result is shown in Table 6.

TABLE 6

| Moisture content (unit: %) versus isosorbide dinitrate content (unit: mg) as time passes | | | | | | | |
|---|---|---|---|---|---|---|---|
| Time passed (hrs) | 0 | 1 | 3 | 6 | 9 | 12 | 24 |
| Moisture content | 2.1 | 1.7 | 1.2 | 0.8 | 0.6 | 0.6 | 0.6 |
| Isosobide dinitrate content | 49 | 19 | 38 | 49 | 51 | 49 | 49 |

Table 6 shows apparently that the medicine isosorbide dinitrate scarcely evaporated while moisture rapidly evaporated away.

It may be assumed that this phenomenon releases the user of the plaster of this invention from contact-type dermatitis.

EXAMPLE 7

A plaster was prepared according to Example 5, except for the use of a hollow fiber specimen containing monoglycolate salicylate and menthol prepared by allowing 10 parts of the hollow fiber specimen (1) to be soaked with 1.2 parts of monoglycolate salicylate and 1.2 parts of menthol, followed by air-drying, instead of the hollow fiber specimen containing isosorbide dinitrate.

Thus prepared plaster was cut into pieces of 6 cm×8 cm size and applied to the skin of healthy adults where they continued to give a refreshing cool feeling showing antiinflammatory and analgesic effects for more than a day.

EXAMPLE 8

A plaster was obtained according to Example 5, except for the use of a hollow fiber specimen containing clenbuterol hydrochloride prepared by allowing 10 parts of the hollow fiber specimen (1) to be soaked with 0.1 part of methanol containing 0.003 part of clenbuterol hydrochloride, followed by air-drying to remove methanol, instead of the hollow fiber specimen containing isosorbide dinitrate.

EXAMPLE 9

A plaster was obtained according to Example 5, except for the use of a hollow fiber specimen containing guaiazulene prepared by allowing 10 parts of the hollow fiber specimen (1) to be soaked with 2 parts of methanol solution containing 0.1 part of guaiazulene, followed by air-drying to remove methanol, instead of the hollow fiber specimen containing isosorbide dinitrate.

EXAMPLE 10

A plaster was obtained according to Example 5, except for the use of a hollow fiber specimen prepared by allowing 10 parts of the hollow fiber specimen (1) to be soaked with polyethylene glycol (molecular weight about 500) containing 0.02 part of 1α,25-dihydroxy vitamin D, instead of the hollow fiber specimen containing isosorbide dinitrate. Also plasters were prepared by using 1α-hydroxy vitamin $D_3$ and 1α,24-dihydroxy vitamin $D_3$ respectively.

INDUSTRIAL APPLICATIONS

This invention relates to a sustained release pharmaceutical plaster which is mainly composed of an adhesive compound layer holding hollow fibers that are made to contain medicines in the tubular hollows of specific type of hollow fibers and a supporter which is to support said adhesive layer. The sustained release pharmaceutical plaster of this invention is highly excellent in the sustained release of medicines and rarely causes sweaty stuffiness and contact-type dermatitis when applied to the human body and can be industrially produced by simple procedures. The plaster of this invention is, therefore, a very useful remedy for various diseases.

We claim:

1. A sustained release pharmaceutical plaster which is characterized in that it is a pharmaceutical preparation comprising an adhesive compound layer and a supporter which supports the adhesive compound layer, inside of which there is an arrangement of hollow fibers, that have radially arranged open pores, with their tubular hollows filled with medicines, wherein 10% to 95% of the total surface area of all the filaments of the hollow fibers do not adhere to the adhesive compound layer.

2. A sustained release pharmaceutical plaster according to claim 1, wherein said medicines are ones that vaporize or are sublimated when applied to the human body.

3. A sustained release pharmaceutical plaster according to claim 2, wherein said medicines that vaporize or are sublimated when applied to human body are nitric esters of isosorbide, halomethane, chloral hydrate, guaiazulene, methol, camphor, clenbuterol hydrochloride, salicyclic esters, or vitamin $D_3$ derivatives.

4. A sustained release pharmaceutical plaster according to claim 1, wherein said hollow fibers are in the structural form of a woven, knitted, or nonwoven fabric.

5. A sustained release pharmaceutical plaster according to claim 1, wherein said hollow fibers are made from polethylene terphthalate.

6. A sustained release pharmaceutical plaster according to claim 1, wherein said supporter is a film having a thickness of 0.5 micron to 4.9 microns.

7. A sustained release pharmaceutical plaster according to claim 1, wherein said adhesive compound layer is one made of acrylic resins comprising (a) at least 50 to 98 mole % of (meth)acrylic alkyl ester having an alkyl group of carbon number of 4 or more and (b) 2 to 50 mole % of acrylic acid and/or methacrylic acid.

8. A sustained release pharmaceutical plaster according to claim 1, wherein the total residue amount of solvents used in preparation of the plaster remaining in the adhesive compound layer, inclusive of the hollow fibers, is less than 50 ppm of the weight of the adhesive compound layer including the hollow fibers.

* * * * *